United States Patent
Chen et al.

(10) Patent No.: US 6,770,607 B2
(45) Date of Patent: Aug. 3, 2004

(54) VISCOELASTIC CLEANSING GEL WITH MICELLAR SURFACTANT SOLUTIONS

(75) Inventors: Liang Bin Chen, Hoffman Estates, IL (US); Michael Alan Rahn, New York, NY (US); Priscilla LaBonville Walling, Darien, IL (US); Marion Louise Margosiak, North Wales, PA (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 36 days.

(21) Appl. No.: 10/242,390

(22) Filed: Sep. 12, 2002

(65) Prior Publication Data

US 2004/0053797 A1 Mar. 18, 2004

(51) Int. Cl.[7] .............................. C11D 1/02; C11D 1/94; C11D 17/00; A61K 7/075
(52) U.S. Cl. ........................ 510/158; 510/123; 510/125; 510/127; 510/137; 510/336; 510/403; 424/70.19
(58) Field of Search ................................ 510/123, 125, 510/127, 137, 158, 336, 403; 424/70.19

(56) References Cited

U.S. PATENT DOCUMENTS

| | | | |
|---|---|---|---|
| 5,385,729 A | * | 1/1995 | Prencipe et al. ......... 424/70.11 |
| 5,536,332 A | | 7/1996 | Chun |
| 5,908,617 A | | 6/1999 | Moore et al. |
| 5,916,549 A | | 6/1999 | Beauquey et al. |
| 5,965,502 A | * | 10/1999 | Balzer ........................ 510/158 |
| 6,426,326 B1 | | 7/2002 | Mitra et al. |

FOREIGN PATENT DOCUMENTS

| | | | |
|---|---|---|---|
| EP | 0 468 721 A1 | 1/1992 | |
| EP | 0 681 832 A2 | 11/1995 | |
| EP | 0 738 509 A2 | 10/1996 | |
| EP | 0 875 236 A2 | 11/1998 | |
| EP | 1 043 010 A2 | 10/2000 | |
| GB | 2280906 A | 2/1995 | |
| GB | 2280906 * | 2/1995 | ........... C11D/17/00 |
| WO | 01/38475 A1 | 5/2001 | |

OTHER PUBLICATIONS

International Search Report Application No. PCT/EP 03/08578 mailed Dec. 4, 2003.

* cited by examiner

Primary Examiner—Brian P. Mruk
(74) Attorney, Agent, or Firm—Milton L. Honig

(57) ABSTRACT

A viscoelastic cleansing gel composition which includes:

a. from about 4 to about 25% an anionic surfactant; and
b. from 0 to about 20% of an amphoteric surfactant;
  wherein the composition has a $G'_h$ at 63 rad/s in a range of about 500 to about 1000 Pa. and a $\omega_c$ in a range of about 0.1 to about 2 rad/sec and;
  wherein the ratio of anionic to amphoteric surfactant is in the range of about 1:3 up to a composition which has anionic but no amphoteric surfactant.

34 Claims, 3 Drawing Sheets

VISCOELASTIC CLEANSING GEL WITH MICELLAR SURFACTANT SOLUTIONS

BACKGROUND OF THE INVENTION

Often children and infants do not enjoy taking a bath. For many years various types of floating toys have been introduced into the bathtub so as to interest children and infants while they are taking a bath.

It would be desirable to develop other ways of entertaining children and infants while they are taking a bath.

The present invention provides hair shampoos and body wash gels which have a consistency such that they jiggle like gelatin, and yet they can hold a shape. In fact these compositions can be molded into various shapes that are of interest to children and infants. Such shapes may include ducks, fish, birds, dinosaurs, planes, trains, and the like.

Such jiggly and shaped hair shampoos and body wash gels are of interest to children and infants who can play with these hair shampoos and body wash gels and even mold these hair shampoos and body wash gels, themselves, before these compositions dissolve in water and release cleansing surfactant. As such these hair shampoos and body wash gels cause children to better enjoy taking a bath or even a shower. It will of course, also be appreciated that the compositions of the invention may be employed by adults.

The compositions of the invention can be packaged in no drip plastic cups. The compositions of the invention can be individually packaged so as to avoid the use of multiple bottles in the shower or bathroom. The compositions of the invention also appear to be effective and concentrated because they can come in individual shapes.

The compositions of the invention which can be characterized as gels or semisolids or viscoelastic compositions, can have more appeal than conventional bar soaps, in that the compositions of the invention tend to lather more easily than conventional bar soaps, and also tend to form a richer lather than conventional bar soaps.

The following is a list of patents and patent applications and a commercial product that relate to the field of the invention.

U.S. Pat. No. 6,426,326 discloses to liquid cleansing compositions in lamellar phase which possess a lotion-like appearance conveying signals of enhanced moisturization. However, these liquids often undergo an irreversible decrease in viscosity under freeze/thaw conditions, losing their moisturization signals. The use of low salt levels in amphoteric and anionic surfactants in a structured liquid product has been found to improve its freeze/thaw stability.

WO 01/38475 discloses a product for use in a fabric laundering process which is in the form of a self-supporting aqueous gel and which comprises one or more fabric treating agents, a gelling agent and one or more surfactants comprising a polypeptide or polysaccharide.

EP 0875236 discloses an aqueous composition for treating keratin fibers, especially human hair, which comprises natural and/or synthetic ingredients with a food or pleasurable aroma and a bitter and with a molecular weight of 250 g/mole which is 10 mg/l soluble in the formulation at 20 degrees C.

JUNGLE GEL is a commercial product which comprises:
about 86.4% water;
about 9.1 % sodium lauryl ether sulfate; and
about 1.5% PEG pentaerythrityl tetrastearate, as well as fragrances, moisturizing oils, colors, and preservatives.

Canadian Application No. 2,194,442 discloses hydrogels which are used as a suitable application form for using active substances in the treatment of skin injuries and/or for the cosmetic treatment of sensitive sites on the skin and nails. These hydrogels are sheet-like, rigid elastic structures adapted to the contours of human body sites and comprise therapeutic and/or cosmetic active substances.

U.S. Pat. No. 5,865,502 discloses aqueous, viscoelastic surfactant solutions for the cleaning of hair and skin which contain:

(A) from 4 to 25% by weight of an anionic surfactant;
(B) from 0 to 10% by weight of a betainic surfactant;
(C) from 0 to 20% by weight of a nonionic surfactant;
(D) from 0 to 6% by weight of an electrolyte;
(E) from 0 to 5% by weight of a water-soluble polymer; and
(F) from 0 to 5% by weight of a further constituent;

in which the sum of the amounts of (A), (B), and (C) is at least 10% by weight and the sum of the amounts of (C), (D), and (E) is between 2 and 20% by weight, in each case based on the total weight of the aqueous solution, and having a shear modulus, $G_0$, between 50 and 500 Pa at temperatures between 20 and 40. degree. C. and a pH of from 4 to 8, and in which the conditions for the identity of the storage modulus, G', and the loss modulus, G", are in the angular frequency range between 0.1 and 60 rad.multidot.s.sup.−1, exhibit optimum flow behavior for the intended applications.

GB 2,280,906 discloses a shaped toiletry product which comprises a gel comprising a gelling agent, preferably up to 15% gelatin, water and at least one surfactant. The surfactant is retained in the gel and is released on contact with warm water. The use of a gel of suitable composition enables toiletry products that are typically in liquid form, for example, bath gels, shower gels and shampoos to be made in a shaped stable form.

SUMMARY OF THE INVENTION

The present invention relates to a viscoelastic cleansing gel, comprising:

a. about 4 to about 30 % an anionic surfactant; and
b. 0 to about 20% of an amphoteric surfactant;
    wherein said composition has a $G'_h$ at about 63 rad/s in the range of about 100 to about 2000 Pa.; a G'/G", $\omega_c$, in the range of about 0.01 to 10 rad/sec; and wherein the ratio of anionic to amphoteric surfactant is in the range of about 1:3 to 100:0, or said another way, said composition has a ratio of anionic to amphoteric surfactant which is in the range of about 1:3 up to a composition which has anionic surfactant and no amphoteric surfactant.

The present invention also relates to a method for cleansing the hair or skin which comprises applying to the hair or skin a viscoelastic cleansing gel as described herein.

DETAILED DESCRIPTION OF THE INVENTION

Unless indicated otherwise, as used herein, "%" means weight %. The starting materials set forth herein are either known or can be prepared in accordance with known methods. G'/G" or $\omega_c$ at 63 rad/s, are used interchangeably to mean crossover frequency. At "about 63 rad/s", means between 62.5 rad/s and 63.5 rad/s. As used herein "jiggly" motion means to move back and forth in a wiggly manner or in a jerky, or shaky manner.

Figure 1:
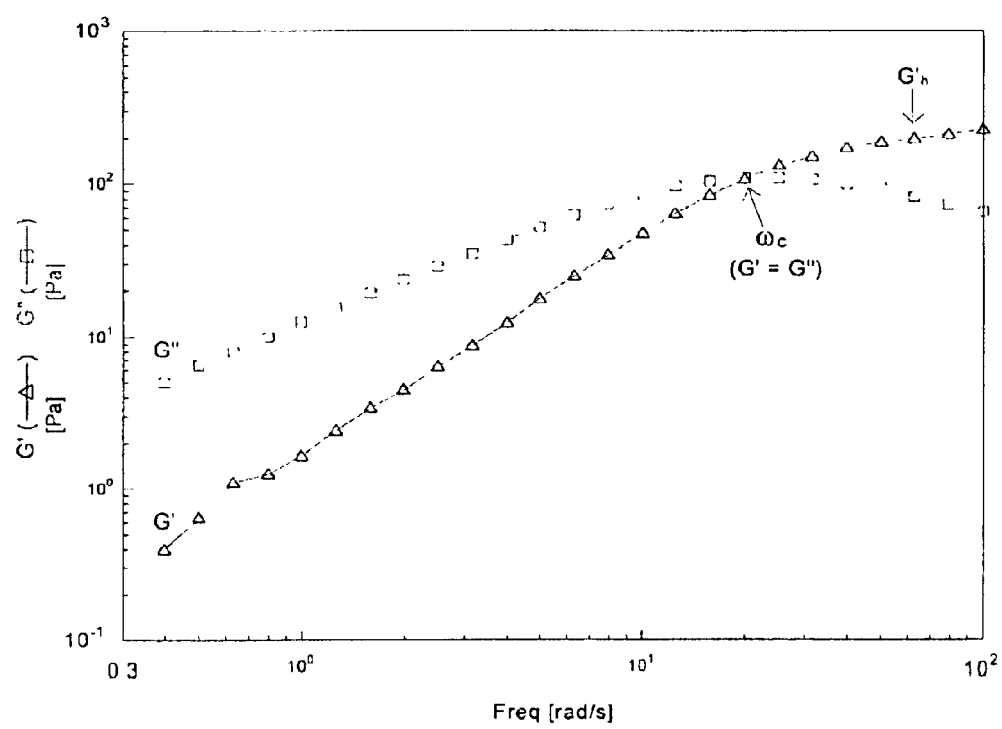
FIG. 1 is a graph of the dynamic oscillatory behavior of a typical micellar cosmetic cleanser that flows like a conventional liquid. The Theological parameter, $G'_h$ and $\omega_c$ are outside the range of the current invention.

Compositions of the invention can exhibit good dissolution rates. The compositions of the invention can also exhibit good dissolution rates after aging (that is, for example, after a long period of storage on a shelf). The methods by which dissolution rates are measured is as follows:

Dissolution Test for Semi-Solid Compositions of the Invention

1) Into a 1000 ml beaker, 600 g water is poured and heated to 105 F.
2) A magnetic stir bar (approximately 1" in length) is added to the beaker and used to stir the liquid. The rotation rate of the stir bar is kept at approximately 100 rpm.
3) A 13 g sample is taken from a mold that is approximately 1¼"×1¼"×½. If sample weighs too much, slices of product are taken from the side until it reaches the desired weight.
4) The sample is dropped into the water and time is started.
5) Dissolution time is amount of time for the sample to dissolve completely.

If a flocculation forms during the dissolving process and the flocculant never dissolves, then the dissolution time is the point at which nothing else dissolves and a note is made that a flocculant has formed.

Mixed anionic/amphoteric or anionic/nonionic surfactant solutions are of great importance in a wide range of industrial and consumer products. The flow properties of these systems affect the manufacturing process, package selection and consumer perception of the products. These surfactants, which can organize themselves into different microstructures, may also exhibit viscoelastic properties. For cosmetic cleansers such as currently marketed shampoos and body wash liquids, the surfactant systems are in the normal micellar ($L_1$) region of the phase diagram. These systems are composed of elongated and rod-like micelles, which exhibit entangled polymer-like flow behavior because of their length and flexibility. The viscoelastic behavior of these cosmetic cleansers can be either described by the Maxwell model or other models that deviate from the Maxwell model (see H. Hoffman and H. Rehage, in *Surfactant Solutions, New Methods of Investigation*; R. Zana, Ed.; Marcel Dekker: New York, 1987; Chapter 4, pp.209–239). Micellar solutions that behave like Maxwell fluids can be represented by a single shear modulus ($G_0$) and a single structure relaxation time constant ($\tau$). For those systems that deviate from the Maxwell model, for which some cosmetic cleansers are examples, the viscoelastic response cannot be represented by a single $G_0$ and a single structural relaxation time $\tau$. Cosmetic cleansers in the micellar phase all exhibit a G'/G" crossover frequency, $\omega_c$, where G' (elastic modulus) is equal to G" (loss modulus). Below the crossover frequency, G' is lower than G" and above the crossover frequency, G' is larger than G" and is approximately equal to $G_0$. For the Maxwell model, the crossover frequency can be related to the structural relaxation $\tau$ as below $$\tau = 1/\omega_c$$

and the G' at the crossover frequency, $G'_c$, can also be related to $G_0$ as shown below.

$$G_0 = 2G'_c.$$

The viscoelastic parameters, G', G" and $\omega_c$ can be determined by using dynamic oscillatory measurement. For the present invention, these measurements were made by a Rheometric ARES rheometer with 25 mm cone and plate geometry. The cone angle is 0.1 radians and the gap is 0.051 mm. The measurement is made at 25° C. An angular frequency range of 0.01 to 125 rad/s is applied to the surfactant solutions at 10% strain, which is in the linear viscoelastic region. In order to compare the elastic component of the present invention to other non-Maxwell behavior surfactant systems, G' at 63 rad/s is recorded. This is valid for a lot of cosmetic cleansers that exhibit Maxwell behavior because the G' at the high frequency region tends towards the plateau value $G_0$. For the present invention, G' measured at 63 rad/s is labeled as $G'_h$.

Most of current micellar phase cosmetic cleansers have $G'_h$ smaller than 400 Pa and $\omega_c$ greater than 10 rad/s. Low elasticity contributions and high $\omega_c$ allow liquid cleanser to pour out of a container at a reasonable flow rate that is consumer preferred.

However, for the present invention, it has been discovered that when a composition or a cleanser has both a $G'_h$ between 100 and 2000 Pa (preferably from 500 Pa to 1000 Pa) and a $\omega_c$ between 0.01 and 7 rad/s (preferably from 0.1 to 2 rad/s), the cleanser behaves like a semi-solid and retains its shape after being dispensed from a container. A high $\omega_c$ means that the structural relaxation time is small, which implies that the time scale it takes for the cleanser to change from solid-like behavior to liquid is short and essentially the cleanser will flow like a conventional liquid. On the other hand, a low $\omega_c$ implies a longer time scale for the cleanser to change from solid-like to liquid, which allow the cleanser to retain its shape shortly after being dispensed from a container. Within these rheological ranges, the surfactant solution exhibits unusual sensory flow characteristics which can be described as, for example, "jiggling", "wiggling" and "wobbling".

Example 1 is a micellar cosmetic handwash liquid using SLS, SLES-2 and cocamidopropyl betaine system that exhibits viscoelastic properties. The viscoelastic profile is shown in FIG. 1. It shows a $G'_h$ lower than 500 Pa and a $\omega_c$ greater than 10 rad/s, as taught in U.S. Pat. No. 5,965,502. This composition flows like a conventional liquid and not like a "jiggle" gel.

EXAMPLE 1

| Ingredients | Weight Percent |
| --- | --- |
| Water | QS |
| Sodium Lauryl Sulfate | 1.7 |
| Sodium Laureth Sulfate (2-mole) | 6.6 |
| Cocamidopropyl Betaine | 2.5 |
| Polyquaternium-10 | 0.15 |

-continued

| Ingredients | Weight Percent |
|---|---|
| Methocel 40–100 | 0.15 |
| Sodium Chloride | 1 |
| Add Fragrance, color and preservatives | * |
| Add NaOH or citric acid to adjust pH | * |
| $\omega_c$ | 21 rad/s |
| $G'_h$ | 199 Pa |

*Added as needed.

The present invention relates to compositions which have viscoelastic ranges for micellar surfactant solutions necessary to ensure optimum shape retention with good dissolution and foaming properties. The rheological parameters $G'_h$ and $\omega_c$ are distinguishing characteristics of the compositions of the invention. Controlling the concentration of the surfactants allows assembly of the surfactants into non-micellar gel phases. Addition of water soluble polymer can also maintain the surfactants as a gel phase.

Surfactant molecules in solution will assemble into different microstructures. When there is sufficient surfactant to form micelles (concentrations above the critical micelle concentration or CMC), for example, spherical, cylindrical or rod-like micelles may form. As surfactant concentration increases, ordered liquid crystalline phases such as the lamellar phase (see Tiddy, G. J. T. *Physics Reports* 1980, 57, 1–46; Tiddy, G. J. T; Walsh, M. F. In *Aggregation Processes in Solution*, Wyn-Jones, E.; Gormally, J., Eds., Elsever, Oxford; 1983, Chapter 7.), the hexagonal phase (see Kilpatrick, P. K; Khan, S. A; Tayal, A; Blackburn, J. C. in *Structure and Flow in Surfactant Solution*, Herb, C. A; Prudhomme, R. K., Eds., ACS Symposium Series 578, ACS, Washington, DC, 1994, Chapter 15) or the cubic phase (see Rosevear, F. B. *J. Soc. Cosmet Chem.*1968, 19, 581; Gradzielski, M; Hoffman, H. In *The Structure, Dynamics and Equilibrium Properties of Colloidal Systems*; Bloor, D. M.; Wyn-Jonesm E., Eds.; Kluwer Academic Publishers: 1990, p. 427) may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. The present invention relates to compositions with viscoelastic properties that are dominated by the cylindrical or rod-like micellar phase.

U.S. Pat. No. 6,426,326 relates to liquid cleansing compositions in lamellar phase which possess a lotion-like appearance conveying signals of enhanced moisturization. Lamellar phase liquids in oscillating measurements generally have storage modulus (G') fairly independent of frequency and always larger than the loss modulus (G").

Figure 2:
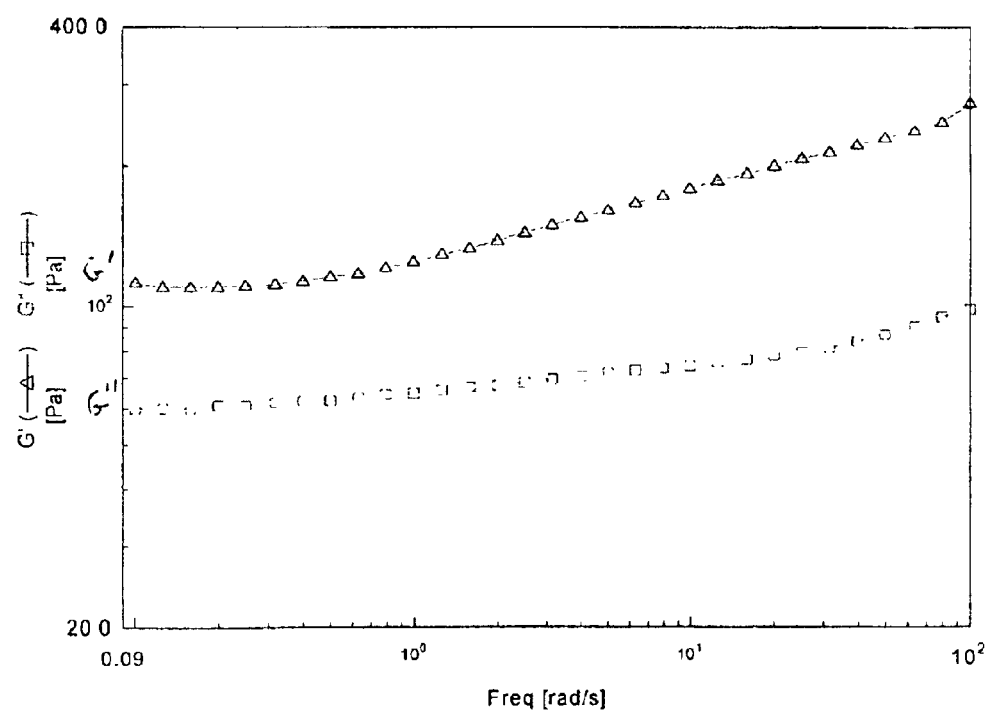
FIG. 2 is a graph showing the dynamic oscillatory behavior of a structured liquid body wash gel in the lamellar phase. The G' is always larger than the G" and there is no crossover frequency.

Example 2 is a structured liquid body wash in the lamellar phase using SLES-3, Cocamide MEA, cocamidopropyl betaine and lauric acid system. The viscoelastic profile of example 2 is shown in FIG. 2. From the angular frequency range of 0.1 to 100 rad/s, both the elastic (G') and the loss (G") moduli depend much less on the frequency than in the micellar phase which is characteristic of the compositions of the invention. In addition, G' is much larger than G" over this frequency range and there is no crossover frequency.

EXAMPLE 2

| Ingredients | |
|---|---|
| Water | Qs |
| SLES-3 | 12% |
| Cocamide MEA | 2% |
| Cocamidopropyl Betaine | 6% |
| Lauric Acid | 2.8% |
| Moisturizing oil (e.g. sunflower seed oil, petrolatum or mineral oil) | 25% |
| Add Fragrance, color and preservatives | * |
| Add NaOH or citric acid to adjust pH | * |
| $\omega_c$ | No crossover |
| $G'_h$ | 240 Pa |

*Added as needed.

Another way to enhance the viscoelastic properties of the surfactant solution is the incorporation of water soluble polymer. The most common polymers used in cosmetic cleansers are hydrocolloids which are hydrophilic polymers of vegetable, animal, microbial or synthetic origin (see R. L. Whistler and J. N. BeMiller, *Industrial Gum: Polysaccharides and their Derivatives*, Academic Press, 1993). These polymers generally contain many hydroxyl groups and may be polyelectrolytes. Examples include but not limited to agar, carrageenan, polyvinyl alcohol, gellan gum and xanthan gum. Most of the hydrocolloids that are of biological origin, have the ability to form reversible gels which melt when heated but revert to a gel when subsequently cooled. One well known example of a hydrocolloid which forms reversible gel is gelatin.

In the current invention, the viscoelastic properties are dominated by the micellar network. These viscoelastic behaviors can be further enhanced with the incorporation of the hydrocolloid, however, the amount the hydrocolloid has to be controlled in order not to change the viscoelastic behavior from the temporary network of the micellar solution to a physically crosslinked network of a gel. The main parameters that distinguish a micellar solution dominated rheology from other types of networks are the crossover frequency, $\omega_c$, and the plateau modulus at high frequency, $G'_h$.

Figure 3:
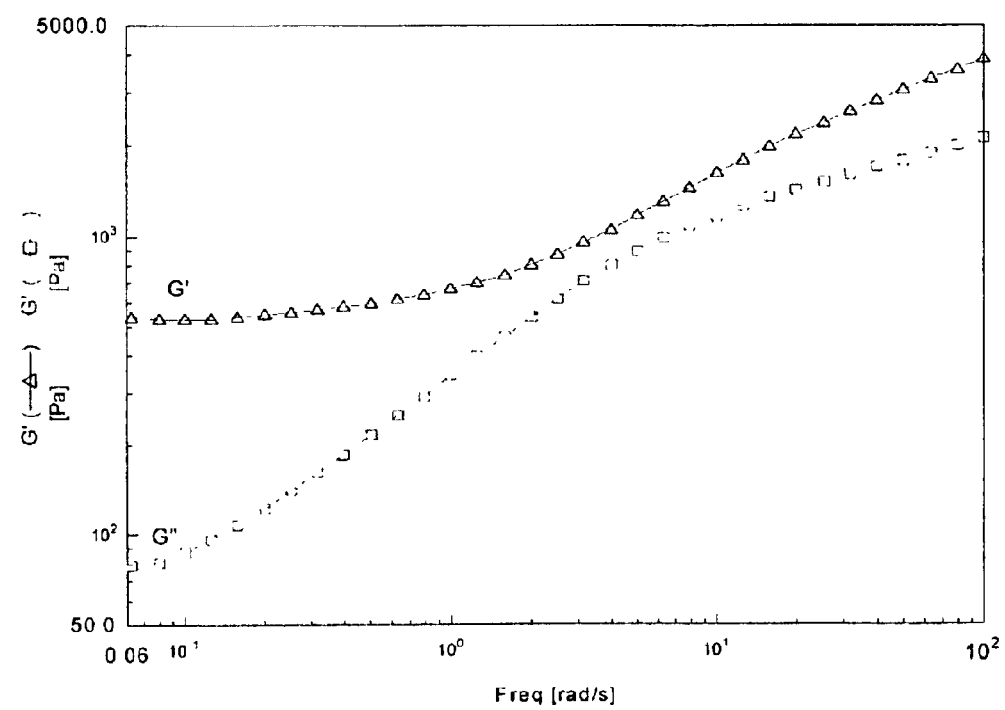
FIG. 3 is a graph showing the showing the dynamic oscillatory behavior of a cosmetic cleanser structured with gelatin. The G' is always larger than the G" and there is no crossover frequency.

Example 3 is a cleanser product using a recipe similar to example 5 from GB 2280906A. The viscoelastic properties are shown in FIG. 3. The G' is much larger than G" and there is no crossover frequency from 0.01 to 100 rad/s. This indicates the gel network form of this composition is more permanent or dominant than the micellar network.

EXAMPLE 3

| Ingredients | Weight percent |
|---|---|
| Water | q.s. |
| Gelatin (Bloom 250) | 5% |
| SLES-2 | 15.3% |
| Cocamide MEA | 5% |
| Glycerine | 10% |
| $\omega_c$ | No crossover |
| $G'_h$ | 3315 Pa |

The present invention provides hair shampoos or body wash gels which have a consistency such that they jiggle like gelatin, and yet they can hold a shape. In fact these compositions can be molded into various shapes that are of interest to children and infants. Such shapes as indicated above, may include ducks, fish, birds, dinosaur, planes, trains, and the like.

Such jiggly and shaped hair shampoos and body wash gels are of interest to children and since children and infants can play with these hair shampoos and body gels and even mold these hair shampoos and body gels before they dissolve in water and release cleansing surfactant. As such these hair shampoos and body gels cause children to better enjoy taking a bath or even a shower. It will of course, also be appreciated that the compositions of the invention may be employed by adults.

It will further be appreciated that the gels or semisolids or viscoelastic compositions of the invention can have more appeal than conventional bar soaps, in that the compositions of the invention tend to lather more easily than conventional bar soaps, and also tend to form a richer lather than conventional bar soaps.

What now follows is a detailed description of each ingredient which may be included in the compositions of the present invention.

Anionic Surfactants

Suitable anionic surfactants are the alkyl sulfates, alkyl ether sulfates, alkaryl sulfonates, alkaryl isethionates, alkyl succinate, alkyl sulfosuccinates, N-alkoyl sarcosinates, alkyl phosphates, alkyl ether phosphates, alkyl ether carboxylates, and alpha-olefin sulfonates, especially their sodium, magnesium, ammonium and mono-, di- and triethanolamine salts. The alkyl and acyl groups generally contain from 8 to 18 carbon atoms and may be saturated and/or unsaturated. The alkyl ether sulfates, alkyl ether phosphates and alkyl ether carboxylates may contain from 1 to 10 ethylene oxide or propylene oxide units per molecule, and preferably contain 1 to 3 ethylene oxide units per molecule. Other suitable anionic surfactants include sodium oleyl succinate, amidosulfur succinate, ammonium lauryl sulfosuccinate, ammonium lauryl sulfate, sodium dodecylbenzene sulfonate, triethanolamine dodecylbenzene sulfonate, sodium cocoyl isethionate, sodium lauroyl isethionate and sodium N-lauryl sarcosinate. The most preferred anionic surfactants are sodium lauryl sulfate [SLS], ammonium lauryl sulfate [ALS], sodium lauryl ether sulfate with 1 EO, 2EO and 3EO [SL(EO)$_{1-3}$S] and ammonium lauryl ether sulfate with 1 EO, 2EO and 3EO [AL(EO)$_{1-3}$S].

Nonionic Surfactants

The nonionic surfactants suitable for use in the compositions of the invention may include condensation products of aliphatic (C8–C18) primary or secondary linear or branched chain alcohols, phenols, esters, acids and amines. Other suitable nonionics include mono or dialkyl alkanolamides or alkyl polyglucosides. Examples include coco mono or diethanolamide, coco mono isopropanolamide, and coco di glucoside.

The cleansing gels of the invention may include a nonionic surfactant is selected from PEG 150 Distearate, cocamide mea, cocamide DEA, and mixtures thereof.

The nonionic surfactant may be selected from the group consisting of a.

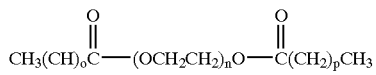

where n has values from 6 to 200, o and p each independently have values of 10 to 18.

Nonionic surfactants can include molecular structures similar to a) above such as PEG Dilaurate, PEG Dioleate, PEG Dipalmitate, PEG Ditallate.

b.

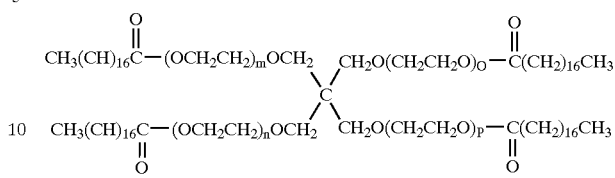

where m+n+o+p=150.

c.

where R could represent the fatty group derived from coconut oil or $CH_3(CH_2)_n$ where n has values of 6 to 16, preferably 10.

d. It could also has structure similar to Cocamide DEA:

where R could represents the fatty group derived from coconut oil or $CH_3(CH_2)_n$ where n has values of 6 to 16, preferably 10.

e. Or mixtures thereof.

Electrolytes

The compositions of the invention may further comprise an electrolyte in a concentration range of about 0.01 to 5% by wt. Suitable electrolytes are salts such as which sodium chloride and ammonium chloride but can also be magnesium chloride, sodium sulfate and also alkali metal salts of carboxylic acids such as sodium citrate.

Amphoteric Surfactants

The amphoteric surfactants suitable for use in the compositions of the invention may include alkyl amine oxides, alkyl betaines, alkyl amidopropyl betaines, alkyl sulfobetaines, alkyl glycinates, alkyl carboxy glycinates, alkyl ampho propionates, alkyl amidopropyl hydroxysultaines, acyl taurates and acyl glutamates wherein the alkyl and the acyl groups have from 8 to 18 carbon atoms. Examples include lauryl amine oxide, cocodimethyl sulfopropyl betaine and preferably lauryl betaine, cocamidopropyl betaine (CAPB), amphoacetate, cocamidopropyl hydroxysultaine and sodium cocamphopropionate.

The cleansing gels of the invention can have an amphoteric surfactant selected from the group consisting of cocamidopropyl betaine and cocamidopropyl hydroxysultaine.

In the present invention, water soluble polymers, such as hydrocolloids, will serve to enhance both $G'_h$ and $\omega_c$ without significantly modifying the viscoelastic behaviors. Incorporation of the hydrocolloids will not change the viscoelastic behavior from the temporary network of the micellar solution to a physically crosslinked network of a gel. Hydrocolloids are hydrophilic polymers, of vegetable, animal, microbial or synthetic origin, that generally contain many hydroxyl groups and may be polyelectrolytes. Examples of bio/natural polymers are polysaccharides such as agar, carrageenan, gellan gum and xanthan gum. A protein base biopolymer such as gelatin is also suitable to use for the current invention. Synthetic polymer includes polyvinyl alcohol or carbomer. Hydrocolloid used in this current invention can be in the range of about 0.01 to 3% by wt. (preferably about 0.5 to 2).

Water

Water is also included in the compositions of the present invention.

The compositions of the present invention can come in individual shapes and sizes. Each individual shape can be molded and packaged into similarly shaped plastic cups. A number of such cups may be adhered to a piece of cardboard, and sold together on that cardboard. Shapes packaged in plastic cups may also be packed inside a box, for example. Compositions of the invention may also be packaged in a can or tub, and the consumer may be provided with scoops or spoons of varying shapes and sizes which can be used to remove compositions of the invention from the can or tub. Compositions of the invention can be molded in the hands by the child or infant who is using it. Compositions of the invention may also be dissolved in water to form a thick and rich lather for the skin and the hair. Compositions can also come in different colors so as to interest children and infants. Compositions can also contain glitter, pearlescing agents, beads, and small toys so as to interest children and infants. Compositions of the invention of course dissolve in the bath water so that when beads and small toys are included in said compositions, they remain with the child or infant after dissolution of the gel. The infant or child can then play with the toys or beads that remain. Compositions of the invention can also contain an amount of a harmless but bitter tasting ingredient, such as about 0.1 to about 0.2% bitrex, so as to prevent children and infants from eating the compositions of the invention.

EXAMPLES

Examples 1, 2, 4 to 8 are not compositions of the invention but instead are seven examples of currently marketed shampoos, shower gel, hand wash liquid and body wash liquids that have rheological parameters $G'_h$ and $\omega_c$ outside those of compositions of the invention. Examples 1 and 2 are the hand wash liquid and the body wash gel that were mentioned above, respectively. The structured liquid body wash gel of Example 2 shows has a frequency range of 0.01 to 100 rad/s, there is no crossover of G' and G". The Kid shampoo has a crossover frequency that is too large to be measured by the rheometer. For the rest of the compositions, their Theological properties are out of the ranges specified for the compositions of the present invention. They all appear to be very flowable.

Example 4 is a currently marketed micellar phase shower gel using Ammonium Lauryl/Laureth sulfate, cocamide MEA and cocamidopropyl betaine.

EXAMPLE 4

| Ingredients | |
| --- | --- |
| Water | Qs |
| Ammonium Lauryl Sulfate | 3.8 |
| Ammonium Laureth Sulfate | 2.7 |
| Cocamide MEA | 0.65 |
| PEG-5 Cocamide | 0.35 |
| Cocamidopropyl Betaine | 0.85 |
| Carbomer | 0.4 |
| Add Fragrance, Color and Preservatives | * |
| Add NaOH or Citric Acid to Adjust pH | * |
| $\omega_c$ | 87 rad/s |
| $G'_h$ | 263 Pa |

*Added as needed.

Examples 5 and 6 are two currently marketed micellar phase body wash liquids using SLS, SLES-2 and cocamidopropyl betaine.

EXAMPLES 5 and 6

| Ingredients | | |
| --- | --- | --- |
| Water | QS | QS |
| Sodium Lauryl Sulfate | 2.7 | 2.7 |
| Sodium Laureth Sulfate (2-mole) | 9 | 9 |
| Cocamidopropyl Betaine | 4 | 4 |
| Polyquaternium-10 | 0.1 | 0.27 |
| Methocel 40–100 | 0.15 | 0.15 |
| Sodium Chloride | 1 | 0.6 |
| Add Fragrance, Color and Preservatives | * | * |
| Add NaOH or Citric Acid to Adjust pH | * | * |
| $\omega_c$ | 32 rad/s | 46 rad/s |
| $G'_h$ | 299 Pa | 198 Pa |

*Added as needed.

Example 7 is a currently marketed micellar phase shampoo liquid using Ammonium Lauryl/Laureth Sulfate, Cocamide MEA system.

EXAMPLE 7

| Ingredients | |
| --- | --- |
| Water | QS |
| Ammonium Lauryl Sulfate | 5 |
| Ammonium Laureth Sulfate | 4 |
| Cocamide MEA | 1 |
| PEG-5 Cacamide | 0.5 |
| Ammonium Chloride | 1.2 |
| Add Fragrance, Color and Preservatives | * |
| Add NaOH or Citric Acid to Adjust pH | * |
| $\omega_c$ | 34 rad/s |
| $G'_h$ | 130 Pa |

*Added as needed.

Example 8 is a currently marketed micellar phase kid shampoo liquid using Sodium Trideceth Sulfate, cocamidopropyl hydroxysultaine and disodium lauroamphodiacetate.

EXAMPLE 8

| Ingredients | |
| --- | --- |
| Water | QS |
| Sodium Trideceth Sulfate | 19 |
| Cocamidopropyl Hydroxysultaine | 6 |
| Disodium Lauroamphodiacetate | 5 |
| PEG-80 Sorbitan Laurate | 9 |
| PEG-150 Distearate | 1.5 |
| Sodium Laureth-13 Carboxylate | 1 |
| Polyquaternium-10 | .2 |
| Add Fragrance, Color and Preservatives | * |
| Add NaOH or Citric Acid to Adjust pH | * |
| $\omega_c$ | Too large to be measured |
| $G'_h$ | 58 Pa |

*Added as needed.

The final pH of examples 1, 2, 4 to 8 were adjusted to between 5.5 to 6.

Table 1 lists most of well known shampoo the currently sold in the market. It shows that none of the shampoos have both $G'_h$ and $\omega_c$ within the range defined by the current patent. Consequently, they all pour out of a container at a reasonable flow rate that is consumer preferred for conventional shampoos. On the other hand none of these products exhibit the "jiggle" behaviors.

TABLE 1

Shampoos Currently Sold in United States

| Shampoo Name | $\omega_c$ (rad/s) | $G'_h$ (Pa) |
|---|---|---|
| Pantene Pro-V Clarifying Shampoo | 32 | 175 |
| Pantene Pro-V 2-in-1 shampoo + conditioner | 27 | 223 |
| Pantene Pro-V shampoo | 26 | 215 |
| VO5 normal shampoo | 13 | 125 |
| VO5 moisturizing shampoo | 15 | 128 |
| L'Oreal Vive 2 in 1 shampoo and conditioner | 17 | 168 |
| L'Oreal Vive curl-moisture shampoo | 22 | 160 |
| Clairol Herbal Essences shampoo | 18 | 161 |
| Pert plus 2-in-1 shampoo + light conditioner | 28 | 237 |
| Physique amplifying shampoo | 31 | 185 |
| TRESemme Hydrology intense moisture shampoo | 18 | 196 |
| Prell rinse clean shampoo | 43 | 354 |
| Thermasilk Heat Activated Regular shampoo | 48 | 296 |
| Finesse Plus Shampoo and Conditioner | 65 | 206 |
| Head and Shoulders dandruff shampoo | 34 | 209 |
| Johnson's baby shampoo w/detangling formula | Greater than 100 | 54 |
| L'Oreal Kids swim and sport shampoo | Greater than 100 | 28 |
| L'Oreal Kids extra gentle 2-in-1 shampoo | Greater than 100 | 15 |

Preparation of Viscoelastic Surfactant Solution:

Compositions of the invention, which are those that jiggle, are prepared by mixing the components in the amounts indicated in the tables. Water is first added in the mixing chamber. If nonionic is to be included in the compositions, it is added next. If the nonionic surfactants are supplied in solid form, heating can accompany this step. Next the anionic surfactant is added followed by the amphoteric surfactant. Electrolytes can also be added at the end of the process if required. If a hydrocolloid polymer is to be used in the composition, it can be added into the mixing chamber before the anionic surfactant.

The compositions of the invention may be prepared using known starting materials or starting materials which may be obtained by known methods. These compositions were prepared by methods which are known in the art or which are analogous to those known in the art.

Examples below shows how one can make "jiggle" surfactant gels by controlling the interaction of the anionic surfactant and nonionic surfactant. Anionic surfactant mix with non-ionic surfactant at the correct concentration can result in the right rheological parameters that exhibit "jiggle" behaviors.

Compositions which do not exhibit "jiggle" behavior are not compositions of the invention.

Example 9, 10, 11, 12, 13, 14 are surfactant solution made by mixing Sodium Laureth (n=>2) Sulfate (SLES-2), Cocamidopropyl Betain (CAPB) and water. These examples show the effect of concentration of surfactants on both $G'_h$ and $\omega_c$ when the ratio of SLES-2 and CAPB is 1:1. At low surfactant concentration the "Jiggle" behavior disappears.

| | Water (percent) | SLES-2 (percent) | CAPB (percent) | $\omega_c$ (rad/s) | $G'_h$ (Pa) | "Jiggle" behavior |
|---|---|---|---|---|---|---|
| 9 | 75 | 12.5 | 12.5 | 0.31 | 485 | Yes |
| 10 | 77 | 11.25 | 11.25 | 0.56 | 452 | Yes |
| 11 | 79.8 | 10.1 | 10.1 | 0.97 | 377 | Yes |
| 12 | 81.8 | 9.1 | 9.1 | 2.2 | 270 | Yes |
| 13 | 83.6 | 8.2 | 8.2 | 6.8 | 161 | Yes |
| 14 | 85.2 | 7.4 | 7.4 | 42 | 66 | No |

Examples below show how one can achieve "Jiggle" behavior by incorporating electrolytes. These examples show that the "Jiggle" behavior of the surfactant solutions can also be further enhanced by incorporation of electrolytes (e.g. $NH_4Cl$)

| | Water (percent) | SLES-2 (percent) | CAPB (percent) | $NH_4Cl$ (percent) | $\omega_c$ (rad/s) | $G'_h$ (Pa) | Jiggle behavior |
|---|---|---|---|---|---|---|---|
| 15 | 74 | 12.5 | 12.5 | 1 | 0.40 | 522 | Yes |
| 16 | 76 | 11.25 | 11.25 | 1 | 0.46 | 490 | Yes |
| 17 | 78.8 | 10.1 | 10.1 | 1 | 0.55 | 440 | Yes |
| 18 | 80.8 | 9.1 | 9.1 | 1 | 0.65 | 394 | Yes |
| 19 | 82.6 | 8.2 | 8.2 | 1 | 0.77 | 334 | Yes |
| 20 | 84.2 | 7.4 | 7.4 | 1 | 0.96 | 287 | Yes |
| 21 | 85.7 | 6.65 | 6.65 | 1 | 1.2 | 215 | Yes |
| 22 | 87 | 6 | 6 | 1 | 1.8 | 162 | Yes |
| 23 | 88.2 | 5.4 | 5.4 | 1 | 2.6 | 115 | Yes |
| 24 | 89.3 | 4.85 | 4.85 | 1 | 4.6 | 79 | No |
| 25 | 90.3 | 4.35 | 4.35 | 1 | 9.0 | 50 | No |

The examples below show how one can enhance the viscoelastic properties of the surfactant solution by incorporating other types on non-ionic surfactant such as PEG-150 distearate. Examples 26, 27 and 28 clearly show that by adding PEG-1 50 distearate, $G'_h$ is increased while $\omega_c$ is decreased, making the surfactant solution more "Jiggling"

Examples 26, 27 and 28 demonstrate that when PEG 150 Distearate is incorporated in the SLES-2 and CAPB surfactant system, both the $G'_h$ and $\omega_c$ is affected.

| | Water (percent) | SLES-2 (percent) | CAPB (percent) | $NH_4Cl$ (percent) | PEG 150 Distearate (percent) | $\omega_c$ (rad/s) | $G'_h$ (Pa) | "Jiggle" behavior |
|---|---|---|---|---|---|---|---|---|
| 26 | 83.6 | 8.2 | 8.2 | | | 4.2 | 194 | Yes |
| 27 | 82.4 | 8.2 | 8.2 | 1.2 | | 0.82 | 345 | Yes |
| 28 | 81.9 | 8.2 | 8.2 | 1.2 | 0.5 | 0.21 | 620 | Yes |

Examples 29, 30 and 31 demonstrate that when PEG 150 Distearate is incorporated in the Sodium Laureth (n=>3) Sulfate (SLES-3), and CAPB surfactant system, both the $G'_h$ and $\omega_c$ is affected.

|    | Water (percent) | SLES-3 (percent) | CAPB (percent) | NH$_4$Cl (percent) | PEG 150 Distearate (percent) | $\omega_c$ (rad/s) | G'$_h$ (Pa) | "Jiggle" behavior |
|----|------|----|-----|-----|-----|-----|------|-----|
| 29 | 81.8 | 10 | 8.2 |     |     | 63  | 0.78 | No  |
| 30 | 80.6 | 10 | 8.2 | 1.2 |     | 61  | 64   | No  |
| 31 | 80.1 | 10 | 8.2 | 1.2 | 0.5 | 3.1 | 507  | Yes |

Examples below demonstrate that when the SLES-2 and CAPB surfactant system has incorporated therein low amounts of hydrocolloids (e.g. Gelatin), the G'$_h$ is increased significantly, however, the $\omega_c$ is only affected slightly.

|    | Water (percent) | SLES-2 (percent) | CAPB (percent) | NH$_4$Cl (percent) | PEG 150 Distearate (percent) | Gelatin (percent) | $\omega_c$ (rad/s) | G'$_h$ (Pa) | "Jiggle" behavior |
|----|------|-----|-----|-----|-----|---|------|-----|-----|
| 28 | 81.9 | 8.2 | 8.2 | 1.2 | 0.5 |   | 0.21 | 620 | Yes |
| 32 | 80.9 | 8.2 | 8.2 | 1.2 | 0.5 | 1 | 0.23 | 840 | Yes |

Examples 31 and 33 below demonstrate that when the SLES-3 and CAPB surfactant system has incorporated therein, in low amounts hydrocolloids (e.g. Gelatin), the G'$_h$ is increased significantly, however, the $\omega_c$ is only affected slightly.

|    | Water (percent) | SLES-3 (percent) | CAPB (percent) | NH$_4$Cl (percent) | PEG 150 Distearate (percent) | Gelatin (percent) | $\omega_c$ (rad/s) | G'$_h$ (Pa) | "Jiggle" behavior |
|----|------|----|-----|-----|-----|---|-----|-----|-----|
| 31 | 80.1 | 10 | 8.2 | 1.2 | 0.5 |   | 3.1 | 507 | Yes |
| 33 | 79.9 | 10 | 8.2 | 1.2 | 0.5 | 2 | 2.1 | 867 | Yes |

Examples 34 and 35 below of cosmetic cleansers of the invention have both G'$_h$ and $\omega_c$ inside the required rheological ranges and therefore exhibit "jiggle" behavior.

EXAMPLE 34

| Ingredients | Weight Percent |
|---|---|
| DI Water | 82.15 |
| Versene 100 | 0.2 |
| Gelatin 275 | 1 |
| SLES-2 | 8 |
| PEG-150 Distearate | 0.5 |
| CAPB (30%) | 6.5 |
| Citric Acid | 0.1 |
| Kathon CG | 0.05 |
| DMDM Hydantoin | 0.1 |
| Fragrance | 1 |
| Color | 0.4 |
| G$_h$' | 791 Pa |
| $\omega_c$ | 0.16 rad/s |

EXAMPLE 35

| Ingredients | Weight Percent |
|---|---|
| DI water | 79.45 |
| Versene 100 | 0.2 |
| SLES-3 | 10 |
| PEG-150 Pentaerythritol Tetrastearate | 0.5 |
| CAPB | 8.2 |
| Citric Acid | 0.1 |
| Kathon CG | 0.05 |
| DMDM Hydantoin | 0.1 |
| Fragrance | 1 |
| Color | 0.4 |
| G$_h$' | 638 Pa |
| $\omega_c$ | 2.4 rad/s |

From the foregoing, it will be appreciated that although specific embodiments of the invention have been described herein for purposes of illustration, various modifications may be made without deviating from the spirit or scope of the invention.

What is claimed is:

1. A viscoelastic cleansing gel composition, comprising:
   a. about 4 to about 25% an anionic surfactant; and
   b. 0 to about 20% of an amphoteric surfactant;
      wherein said composition has a $G'_h$ at 63 rad/s in the range of about 500 to about 1000 Pa.;
      a $\omega_c$ in the range of about 0.1 to about 2 rad/sec; and
      wherein the ratio of anionic to amphoteric surfactant is in the range of about 1:3 up to a composition which has anionic but no amphoteric surfactant, the composition being a jiggle gel.

2. A composition according to claim 1 which comprises about 6% to about 15% anionic surfactant.

3. A composition according to claim 1 which comprises about 4% to about 12% amphoteric surfactant.

4. A composition according to claim 1 wherein the ratio of anionic to amphoteric surfactant is in the range of about 1:2 to about 5:1.

5. A composition according to claim 1 which further comprises about 0.01% to about 15% of a nonionic surfactant.

6. A composition according to claim 1 which further comprises about 0.5% to about 10% of a nonionic surfactant.

7. A composition according to claim 5 wherein said nonionic surfactant is selected from the group consisting of
   a.
   $$CH_3(CH)_o C\text{—}(OCH_2CH_2)_n O\text{—}\overset{O}{\overset{\|}{C}}(CH_2)_p CH_3$$
   where n has values from 6 to 200, o and p independently have values of 10 to 18;
   b.
   $$\begin{array}{c} CH_3(CH)_{16}\overset{O}{\overset{\|}{C}}\text{—}(OCH_2CH_2)_m OCH_2 \quad CH_2O(CH_2CH_2O)_o\text{—}\overset{O}{\overset{\|}{C}}(CH_2)_{16}CH_3 \\ \diagdown\;\;\diagup \\ C \\ \diagup\;\;\diagdown \\ CH_3(CH)_{16}\overset{}{C}\text{—}(OCH_2CH_2)_n OCH_2 \quad CH_2O(CH_2CH_2O)_p\text{—}C(CH_2)_{16}CH_3 \\ \| \quad\quad\quad\quad\quad\quad\quad\quad\quad\quad\quad\quad\quad\quad\quad\quad\quad \| \\ O \quad\quad\quad\quad\quad\quad\quad\quad\quad\quad\quad\quad\quad\quad\quad\quad\quad O \end{array}$$
   wherein m+n+o+p=150;
   c.
   $$RC\text{—}NHCH_2CH_2OH$$
   where R represents the fatty group derived from coconut oil or $CH_3(CH_2)_n$ where n has values of 6 to 16; and
   d.
   $$R\overset{O}{\overset{\|}{C}}\text{—}N(CH_2CH_2OH)_2$$
   where R represents the fatty group derived from coconut oil or $CH_3(CH_2)_n$ where n has values of 6 to 16;
   e. and mixtures thereof.

8. A composition according to claim 7, the value of n in component c is 10.

9. A composition according to claim 7, the value of n in component d is 10.

10. A composition according to claim 5 wherein said nonionic surfactant is selected from the group consisting of PEG 150 distearate, coamide DEA, and Cocoamide MEA and mixtures thereof.

11. A composition according to claim 1 wherein said anionic surfactant is selected from the group consisting of sodium lauryl sulfate, sodium lauryl ether, sulfate with 1 EO, sodium lauryl ether sulfate with 2 EO, sodium lauryl ether sulfate with 3 EO, alpha-olefin sulfonate, ammonium lauryl sulfate, ammonium lauryl ether sulfate, ammonium lauryl sulfosuccinate, sodium lauryl sulfosuccinate, sodium trideceth sulfate, and mixtures thereof.

12. A composition according to claim 1 wherein said amphoteric surfactant is selected from the group consisting of cocoamido propyl betaine, amphoacetate, cocamidopropyl hydroxysultaine and mixtures thereof.

13. A composition according to claim 1 which further comprises emollients, anti dandruff agents, skin feel agents, hair dyes, styling polymer, silicone oil, cationic polymers and mixtures thereof.

14. A composition according to claim 1 which further comprises a member selected from the group consisting of a glittering agent, a pearlescent agent, a toy, a bead, and mixtures thereof.

15. A composition according to claim 1 which further comprises occlusive emollients selected from the group consisting of triglyceride oil, petroleum oil, a non-occlusive emollient selected from the group consisting of glycerin, polyols, and a member selected from the group consisting of specific skin feel agents, cationic polymers and mixtures thereof.

16. A composition according to claim 1 which further comprises an electrolyte.

17. A composition according to claim 16 wherein said electrolyte is selected from the group consisting of ammonium chloride and sodium chloride.

18. A composition according to claim 16 wherein said electrolyte is present at about 0.01 to 5%.

19. A composition according to claim 1 which further comprises a thickening agent.

20. A composition according to claim 19 wherein said thickening agent is a hydrocolloid.

21. A composition according to claim 20 wherein said hydrocolloid is a hydrophilic polymers.

22. A composition according to claim 21 wherein said hydrocolloid or hydrophilic polymer is selected from the group consisting of agar, carrageenan, polyvinyl alcohol, gellan gum, crosslinked polyacrylates, acrylates/C10–30 alkyl acrylates crosspolymer and xanthan gum.

23. A composition according to claim 20 wherein said hydrocolloid or is in a range of about 0.01 to 3% by wt.

24. A composition according to claim 20 wherein said hydrocolloid or is gelatin.

25. A composition according to claim 21 wherein the hydrocolloid or hydrophilic polymer is between about 0.5 to about 2 percent.

26. A composition according to claim 1 wherein said anionic surfactant is selected from the group consisting of alkyl sulfates, alkyl ether sulfates, alkaryl sulfonates, alkaryl isethionates, alkyl succinate, alkyl sulfosuccinates, N-alkoyl sarcosinates, alkyl phosphates, alkyl ether phosphates, alkyl ether carboxylates, and alpha-olefin sulfonates, sodium oleyl succinate, ammonium lauryl sulfosuccinate, ammonium lauryl sulfate, sodium dodecylbenzene sulfonate, triethanolamine dodecylbenzene sulfonate, sodium cocoyl isethionate, sodium lauroyl isethionate and sodium N-lauryl sarcosinate.

27. A composition according to claim 1 wherein said anionic surfactant is selected from the group consisting of sodium lauryl sulfate, ammonium lauryl sulfate, sodium lauryl ether sulfate with 1 EO, 2EO and 3EO and ammonium lauryl ether sulfate with 1 EO, 2EO and 3EO, and mixtures thereof.

28. A composition according to claim 5 wherein said nonionic surfactant is selected from the group consisting of condensation products of aliphatic ($C_8$–$C_{18}$) primary or secondary linear or branched chain alcohols, phenols, esters, acids and amines, mono or dialkyl alkanolamides and alkyl polyglucosides, and mixtures thereof.

29. A composition according to claim 1 wherein said amphoteric surfactant is selected from the group consisting of alkyl amine oxides, alkyl betaines, alkyl amidopropyl betaines, alkyl sulfobetaines, alkyl glycinates, alkyl carboxy glycinates, alkyl ampho propionates, alkyl amidopropyl hydroxysultaines, acyl taurates and acyl.

30. A composition according to claim 1 wherein the gel has a dissolution time of about 1000 to about 1800 seconds.

31. A composition according to claim 1 wherein the gel has a dissolution time of about 1000 to about 1700 seconds.

32. A composition according to claim 1 which is a micellar (L1) solution.

33. A method for washing hair which comprises applying to the hair a composition according to claim 1.

34. A method for washing skin which comprises applying to the skin a composition according to claim 1.

* * * * *